United States Patent
Colgan et al.

(10) Patent No.: US 11,273,426 B2
(45) Date of Patent: *Mar. 15, 2022

(54) IMAGING MULTIPLE CHEMICAL REACTIONS IN A FLOW CELL ARRAY

(71) Applicant: International Business Machines Corporation, Armonk, NY (US)

(72) Inventors: Evan Colgan, Montvale, NJ (US); Alexey Y. Lvov, Congers, NY (US); Stanislav Polonsky, Putnam Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 382 days.

This patent is subject to a terminal disclaimer.

(21) Appl. No.: 15/833,328

(22) Filed: Dec. 6, 2017

(65) Prior Publication Data

US 2018/0093243 A1   Apr. 5, 2018

Related U.S. Application Data

(62) Division of application No. 14/973,234, filed on Dec. 17, 2015, now Pat. No. 10,583,414, which is a division of application No. 14/170,845, filed on Feb. 3, 2014, now Pat. No. 9,387,451.

(51) Int. Cl.
*B01J 19/00* (2006.01)
*B01L 3/00* (2006.01)
*C12Q 1/6874* (2018.01)

(52) U.S. Cl.
CPC .......... *B01J 19/0046* (2013.01); *B01L 3/502* (2013.01); *B01L 3/5027* (2013.01); *C12Q 1/6874* (2013.01); *B01J 2219/00286* (2013.01); *B01J 2219/00306* (2013.01); *B01J 2219/00418* (2013.01); *B01J 2219/00511* (2013.01); *B01J 2219/00522* (2013.01); *B01J 2219/00527* (2013.01); *B01J 2219/00576* (2013.01); *B01J 2219/00585* (2013.01); *B01J 2219/00596* (2013.01); *B01J 2219/00621* (2013.01); *B01J 2219/00659* (2013.01); *B01J 2219/00689* (2013.01); *B01J 2219/00695* (2013.01); *B01J 2219/00698* (2013.01); *B01J 2219/00702* (2013.01); *B01L 2200/0684* (2013.01); *B01L 2200/10* (2013.01); *B01L 2300/024* (2013.01); *B01L 2300/041* (2013.01); *B01L 2300/0874* (2013.01)

(58) Field of Classification Search
None
See application file for complete search history.

(56) References Cited

U.S. PATENT DOCUMENTS

| | | |
|---|---|---|
| 5,389,196 A | 2/1995 | Bloomstein et al. |
| 5,846,396 A | 12/1998 | Zanzucchi |
| 5,959,098 A | 9/1999 | Goldberg |
| 6,749,814 B1 | 6/2004 | Bergh et al. |
| 7,476,510 B2 | 1/2009 | Kapur et al. |
| 7,604,718 B2 | 10/2009 | Zhang et al. |
| 8,232,108 B2 | 7/2012 | Hartzell et al. |
| 8,487,790 B2 | 7/2013 | Fife et al. |
| 2002/0037499 A1 | 3/2002 | Quake |
| 2003/0008411 A1 | 1/2003 | Van Dam |
| 2003/0138941 A1 | 7/2003 | Gong |
| 2003/0224531 A1 | 12/2003 | Brennen |
| 2005/0079603 A1 | 4/2005 | Sandstrom |
| 2005/0130173 A1 | 6/2005 | Leamon |
| 2005/0196321 A1 | 9/2005 | Huang |
| 2005/0221351 A1 | 10/2005 | Ryu |
| 2006/0006067 A1 | 1/2006 | Unger |
| 2006/0040309 A1 | 2/2006 | Wilding |
| 2008/0242556 A1 | 10/2008 | Cao |
| 2009/0023146 A1 | 1/2009 | Harnack |
| 2010/0233696 A1 | 9/2010 | Joseph |
| 2011/0143964 A1 | 6/2011 | Zhou |
| 2011/0201509 A1 | 8/2011 | Tegenfeldt |
| 2012/0020537 A1 | 1/2012 | Garcia |
| 2012/0052563 A1 | 3/2012 | Liang et al. |
| 2012/0165215 A1 | 6/2012 | Andersen et al. |
| 2012/0190591 A1 | 7/2012 | Wohlstadter et al. |
| 2013/0116153 A1 | 5/2013 | Bowen et al. |
| 2013/0291662 A1 | 11/2013 | Johnson et al. |

FOREIGN PATENT DOCUMENTS

WO   2000004366 A1   1/2000

OTHER PUBLICATIONS

Wang, Lin, and Paul CH Li. "Microfluidic DNA microarray analysis: A review." Analytica chimica acta 687.1 (2011): 12-27.*
Bentley et al. Accurate Whole Human Genome Sequencing Using Reversible Terminator Chemistry, Nature, vol. 456(7218), p. 53-59, 2008.
U.S. Appl. No. 13/920,226, filed Jun. 18, 2013 and entitled "Nanochannel Process and Structure for Bio-Detection."
Zhu et al. Cost-Effective and Compact Wide-field Fluorescent Imaging on a Cell-Phone, Lab Chip, 2011, 11: 315-322 (Year: 2011).
Lipshutz, Robert J., et al. High Density Synthetic Oligonucleotide Arrays. Nature Genetics 21.1 (1999). 20-24.
Margulies, Marcel, et al. Genome Sequencing in Microfabricated High-Density Picolitre Reactors. Nature 437.7057 (2005):376-380.

(Continued)

*Primary Examiner* — G Steven Vanni
(74) *Attorney, Agent, or Firm* — Ryan, Mason & Lewis, LLP

(57) ABSTRACT

Systems, computer program products, and methods for using a flow cell array are provided herein. A computer program product includes a computer readable storage medium having program instructions embodied therewith, the program instructions executable by a device to cause the device to determine placement of multiple reaction site openings, wherein each reaction site opening is connected to a first sub-surface channel; connect the first sub-surface channel to two or more additional sub-surface channels by multiple vias; and provide a material for multiple reaction sites, wherein an overlap of the multiple reaction site openings and the material delineate the multiple reaction sites.

2 Claims, 11 Drawing Sheets

(56) References Cited

OTHER PUBLICATIONS

Rothberg, Jonathan M., et al. An Integrated Semiconductor Device Enabling Non-Optical Genome Sequencing, Nature 475.7356 (2011): 346-352.

* cited by examiner

EXAMPLE FOR n = 6:

IMAGING MULTIPLE CHEMICAL REACTIONS IN A FLOW CELL ARRAY

FIELD OF THE INVENTION

Embodiments of the invention generally relate to information technology, and, more particularly, to biological sequencing.

BACKGROUND

Existing deoxyribonucleic acid (DNA) sequencing techniques, such as sequencing-by-synthesis (SBS), sequencing-by-ligation, and pyro-sequencing, use imaging of parallel cyclical chemical reactions. For example, reversible dye-terminators (RDTs) add one fluorescently-labeled nucleotide to a template (single-stranded DNA, for example) per cycle and determine the type of incorporated nucleotide based on the color of the fluorescent label. Such reactions require changing chemicals at every cycle and rely on fluidic cells to deliver the chemicals to multiple reaction sites. Typically, each cycle of an RDT chemical reaction includes the steps of detritylation, coupling, capping and oxidation, and requires approximately 10-15 minutes. Additionally, the minimum distance between reaction sites is limited by the optical resolution of fluorescent microscopes. Also, reaction sites can be random or regular.

Accordingly, a need exists for decreasing the distance between reaction sites below the optical resolution limit so as to increase the throughput of DNA sequencing.

SUMMARY

In one aspect of the present invention, a pipelined flow cell and related processes are provided. In one aspect of the invention, an exemplary apparatus can include an array comprising one or more pixels, wherein each of the one or more pixels comprises one or more reaction sites; and a network comprising (i) a set of one or more surface channels in a first component of the array, and (ii) a set of two or more sub-surface channels in a second component of the array, wherein each reaction site corresponds to a channel from the set of one or more surface channels, and wherein said set of two or more sub-surface channels comprises one or more sub-surface channels proximate to a first portion of the array and one or more sub-surface channels proximate to a second portion of the array. The apparatus also includes multiple vias in the second component of the array connecting each channel from the set of one or more surface channels to (i) one of the one or more sub-surface channels proximate to the first portion of the array and (ii) one of the one or more sub-surface channels proximate to the second portion of the array.

An exemplary method can include steps of determining placement of one or more reaction sites on a first component; providing a material for the one or more reaction sites in one or more surface channels of the first component; connecting the first component to a second component to form an array, wherein the one or more surface channels of the first component connect the one or more reaction sites with one or more vias, and wherein the second component comprises the one or more vias connected to multiple sub-surface channels; and aligning the one or more surface channels of the first component with the one or more vias of the second component to form a connection between the first component and the second component.

In another aspect of the invention, an exemplary apparatus can include an array comprising one or more pixels, wherein each of the one or more pixels comprises multiple reaction sites openings; a first set of one or more sub-surface channels, wherein each of the multiple reaction site openings is connected to a sub-surface channel from the first set of one or more sub-surface channels; a second set of two or more sub-surface channels; and multiple vias connecting each channel from the first set of one or more sub-surface channels to (i) a first sub-surface channel from the second set of two or more sub-surface channels and (ii) a second sub-surface channel from the second set of two or more sub-surface channels.

Yet another exemplary method can include steps of determining placement of multiple reaction site openings, wherein each reaction site opening is connected to a first sub-surface channel; connecting the first sub-surface channel to two or more additional sub-surface channels by multiple vias; and providing a material for multiple reaction sites, wherein an overlap of the multiple reaction site openings and the material delineate the multiple reaction sites.

Also, in yet another aspect of the invention, an exemplary method can include steps of delivering multiple items of chemical matter independently to multiple reaction sites of a flow cell array across multiple distinct instances of time; imaging multiple parallel chemical reactions at the multiple reaction sites of the flow cell array; and recording an emission from each of the multiple chemical reactions site.

Another aspect of the invention or elements thereof can be implemented in the to form of an article of manufacture tangibly embodying computer readable instructions which, when implemented, cause a computer to carry out a plurality of method steps, as described herein. Furthermore, another aspect of the invention or elements thereof can be implemented in the form of an apparatus including a memory and at least one processor that is coupled to the memory and configured to perform noted method steps. Yet further, another aspect of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an aspect of the present invention includes providing a pipelined flow cell microarray for imaging parallel chemical reactions such as, for example, DNA sequencing. At least one embodiment of the invention includes generating and/or implementing a pipelined pixel flow cell, wherein a number of sub-pixels are formed and chemistry is pipelined in each of the sub-pixels.

Figure 1:
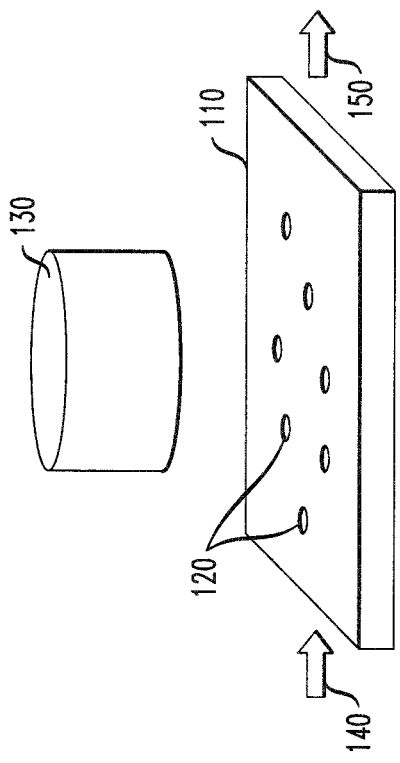
FIG. 1 is a diagram illustrating an existing sequencing setup.

FIG. 1 is a diagram illustrating an existing sequencing setup. By way of illustration, microarray 110, which includes multiple reaction sites 120, is placed under an imaging microscope 130. Chemicals 140 are sent through the microarray 110 and leave the fluidic cell (as illustrated via arrow 150).

Figure 2:
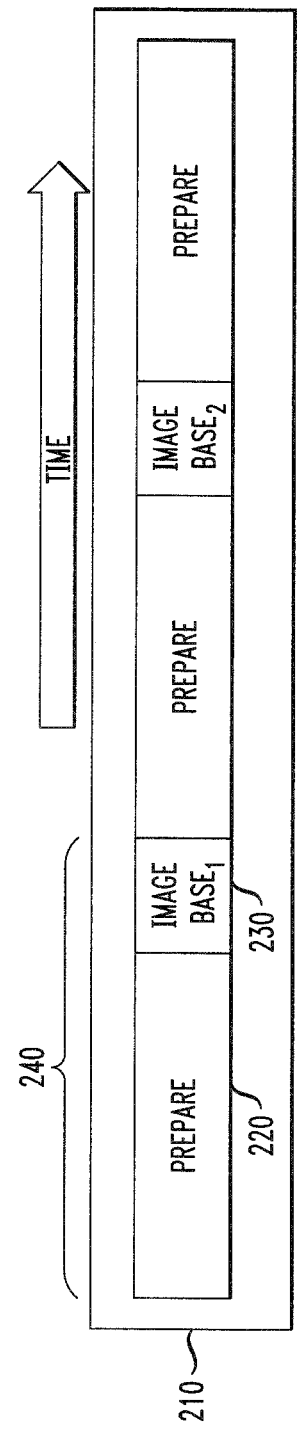
FIG. 2 is a diagram illustrating cycles of a typical sequencing reaction.

FIG. 2 is a diagram illustrating cycles of a typical sequencing reaction 210. During "Prepare" step 220, a set of chemicals is delivered to the fluidic cell and/or microarray (such as microarray 110 in FIG. 1) which causes some of the reaction sites (such as sites 120 in FIG. 1) to become fluorescent. During "Image" step 230, a fluorescent microscope (such as microscope 130 in FIG. 1) images the microarray. The computer analysis of the emission from each reaction site provides information about the DNA sequence. For example, in the case of RDT, the color of the reaction site identifies the type of incorporated nucleotide. In such existing approaches, separating emissions from different test sites is achieved through the use of sufficient distance between reaction sites, whereby the distance should exceed the resolution of the imaging system. Such a concept is referred to herein as space multiplexing.

Referring back to FIG. 2, "Prepare" step 220 and "Image" step 230 comprise the first cycle 240 of the reaction 210. Cycles can be repeated many times, for example, to obtain the sequence of DNA molecules in each reaction site.

Typically, "Prepare" step 220 is much longer in duration than "Image" step 230. Accordingly, this configuration can be used in accordance with at least one embodiment of the invention to implement time multiplexing between reaction sites. Assuming the reaction sites do not fluoresce during "Prepare" steps, an example of such time multiplexing is depicted in FIG. 3.

Figure 3:
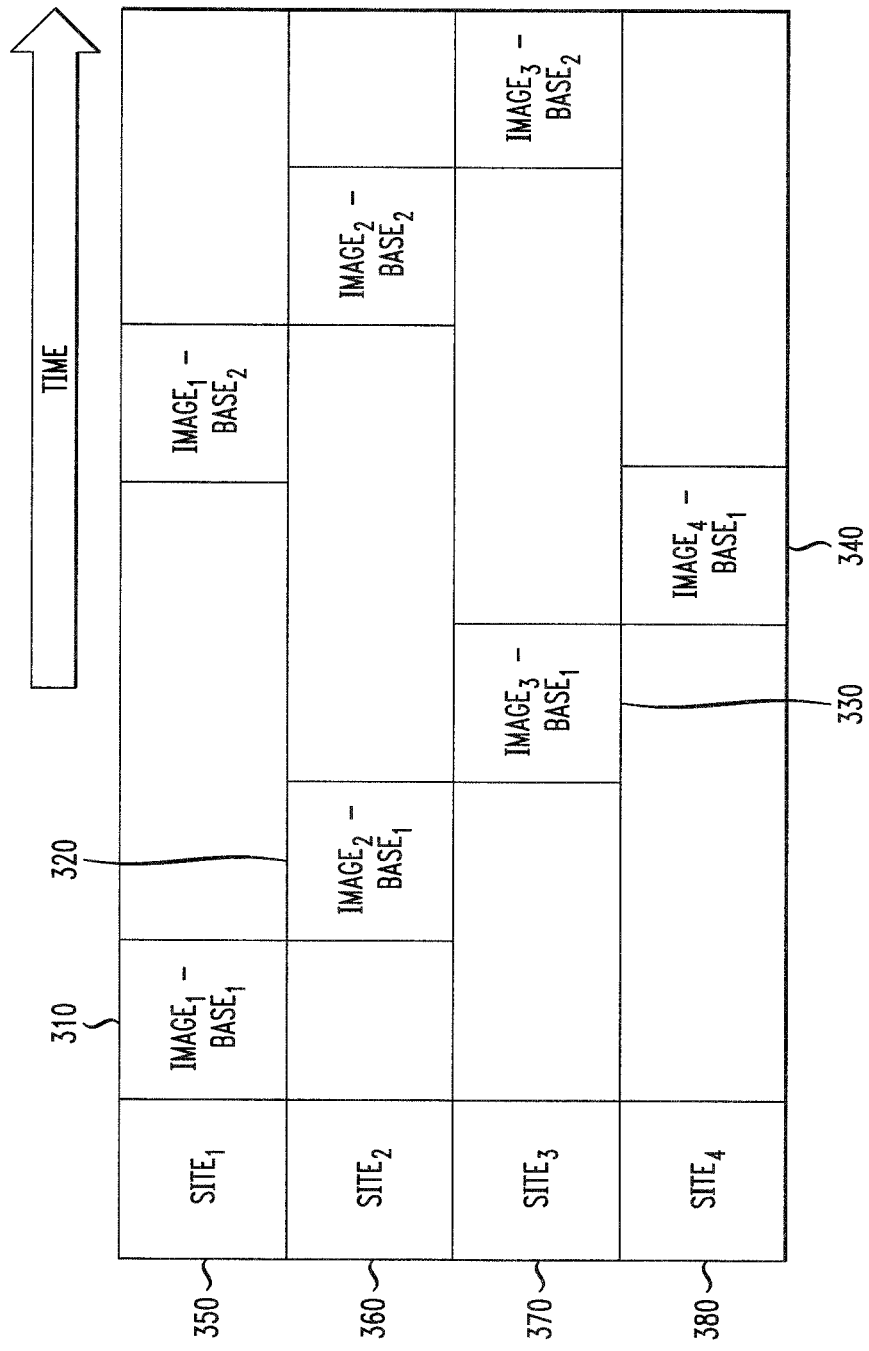
FIG. 3 is a diagram illustrating time multiplexing between reaction sites, in accordance with an example embodiment of the invention.

Accordingly, FIG. 3 is a diagram illustrating time multiplexing between reaction sites, in accordance with an example embodiment of the invention. Sequencing chemistry is independently delivered to each reaction site, namely, Site$_1$ (350), Site$_2$, (360), Site$_3$ (370), and Site$_4$(380) with some time delay. As a result, each reaction site is fluorescent during non-overlapping time intervals, namely, Image$_1$-base$_1$ (310), Image$_2$-base$_1$ (320), Image$_3$-base$_1$ (330), and Image$_4$-base$_1$ (340). Consequently, the emission from each reaction site can be recorded at different time moments and there is no need to separate sites by a sufficiently large distance. In other words, the distance between reaction sites can be made smaller than the optical resolution of imaging system, provided that the chemistry is independently delivered to these sites.

As further detailed herein, at least one embodiment of the invention can begin executing a second instruction before a first instruction has been completed. As a result, several instructions can be in the pipeline at the same time, each at a different execution step.

Figure 4:
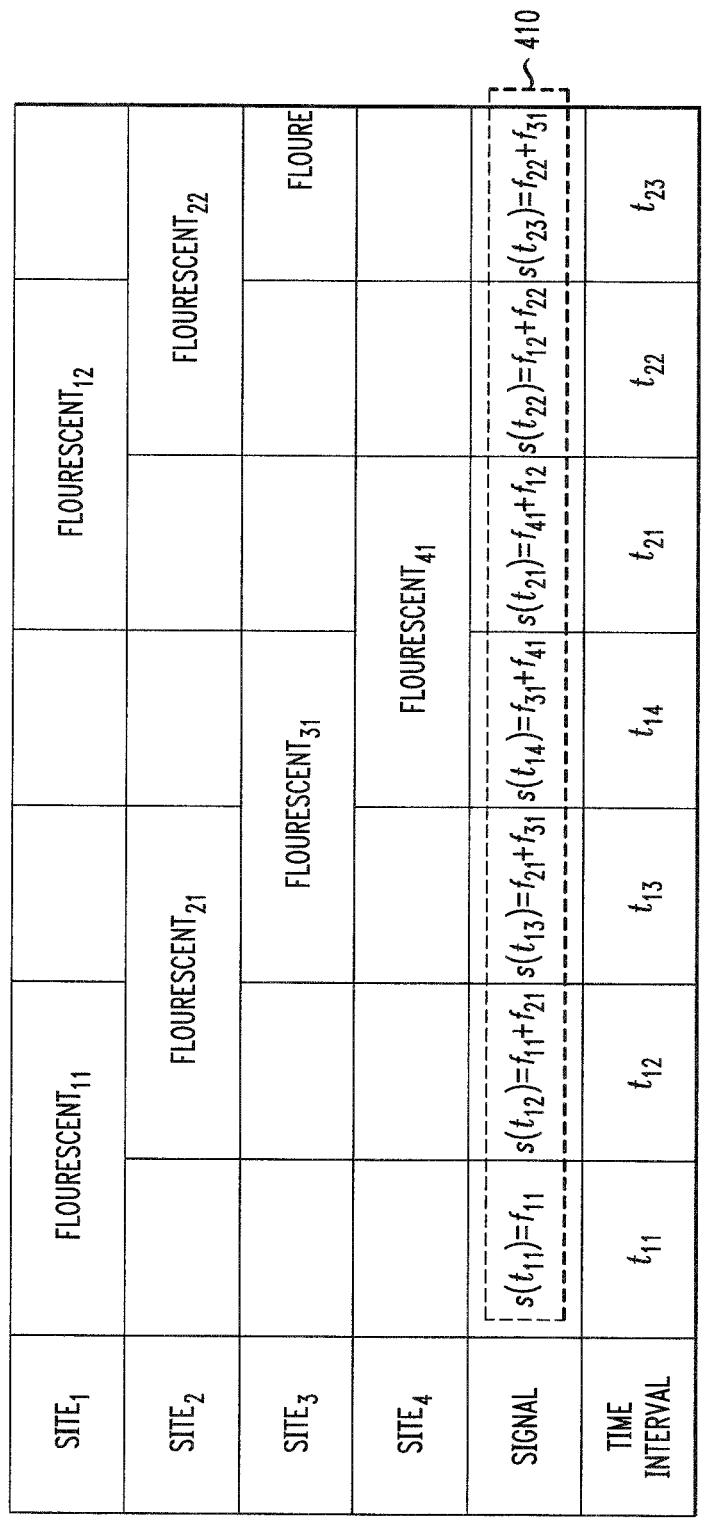
FIG. 4 is a diagram illustrating time multiplexing between reaction sites with overlapping fluorescence at different sites, in accordance with an example embodiment of the invention.

FIG. 4 is a diagram illustrating time multiplexing between reaction sites with overlapping fluorescence at different sites, in accordance with an example embodiment of the invention. By way of illustration, FIG. 4 depicts an example wherein only two sites out of four are fluorescent at any given time moment. By way of example, at time interval $t_{11}$, only site$_1$ is fluorescent, and site$_1$ emits signal $f_{11}$. The measured signal from all four sites is $s(t_{11})=f_{11}$. During time interval $t_{12}$, site$_2$ becomes fluorescent, and site$_2$ emits signal $f_{21}$. The measured signal at this time interval is $s(t_{12})=f_{11}+f_{21}$. During $t_{13}$, site$_1$ stops fluorescence, but site$_3$, in turn, starts to emit signal $f_{31}$. As a result, $s(t_{13})=f_{31}+f_{31}$. Repeated cycling results in a system of equations 410, which can be solved for individual emissions $f_{ij}$ from different sites $i=1 \ldots 4$ at different cycle numbers $j=1, 2, \ldots$ . It is noted that in accordance with at least one example embodiment of the invention, the maximum number of simultaneously fluorescent sites will be limited by dynamic range of the imaging system.

Additionally, at least one embodiment of the invention includes combining space multiplexing and time multiplexing in a pipelined microarray. As used herein, the term "pipelined" refers to a configuration for independently providing instructions to microfluidic channels, as detailed herein.

Figure 5:
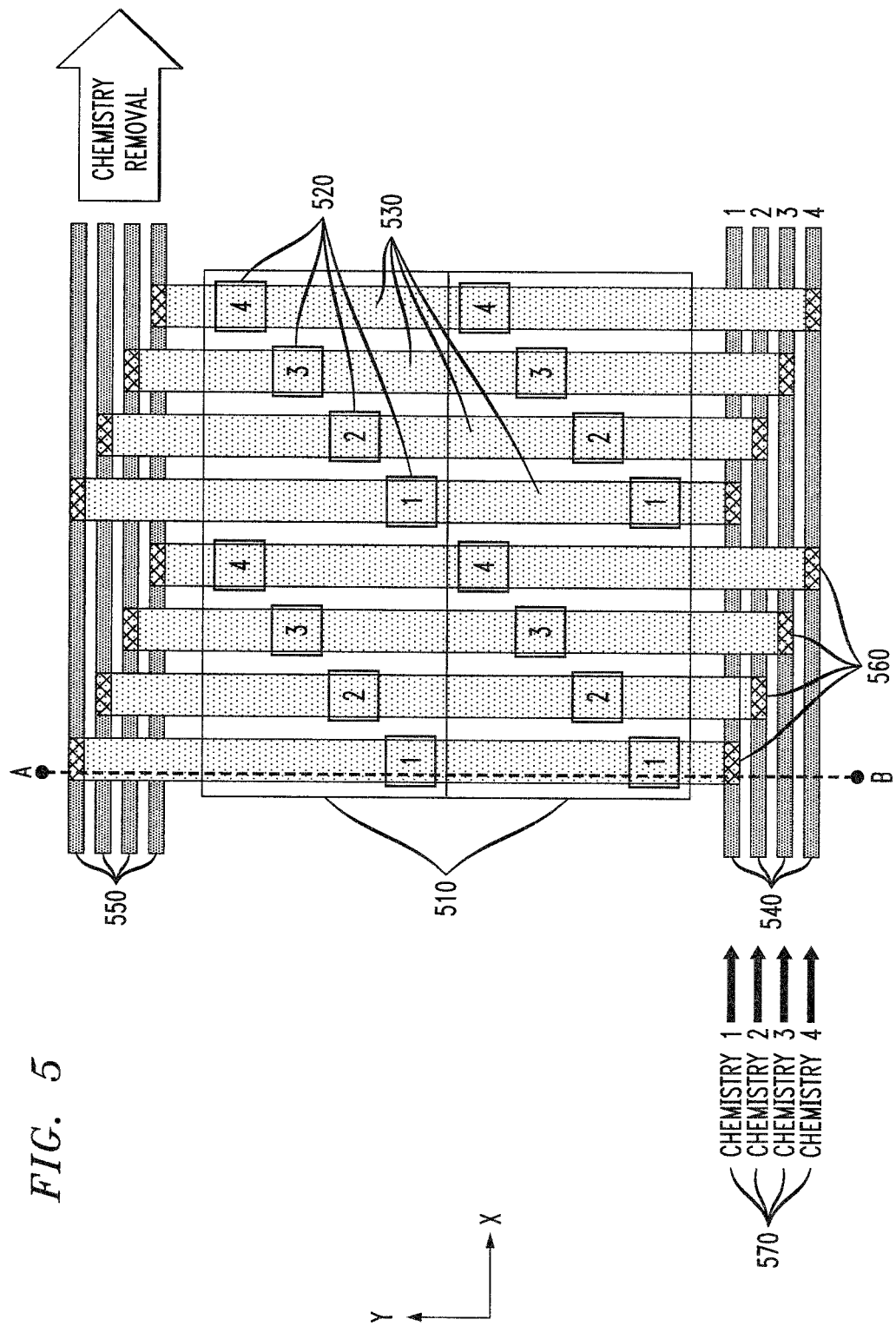
FIG. 5 is a diagram illustrating a top view of a pipelined microarray with individually addressable reaction sites, in accordance with an example embodiment of the invention.

FIG. 5 is a diagram illustrating a top view of a pipelined microarray with individually addressable reaction sites, in accordance with an example embodiment of the invention. In the example embodiment depicted in FIG. 5, the pipelined microarray is organized as an array of pixels 510. In this specific example, a 2×2 array is depicted. It is to be appreciated, however, that this array is being described merely as an example embodiment of the invention, and separate and/or additional configurations can be implemented.

Pixel size can be determined, for example, by the optical resolution of the imaging microscope and can be of the order of a micrometer or larger. Each pixel 510 has multiple reaction sites 520. In this specific example depicted in FIG. 5, four reaction sites 520 are illustrated. It is to again be appreciated, however, that this arrangement is described merely as an example, and separate and/or additional configurations can be implemented in accordance with one or more embodiments of the invention.

Additionally, microfluidic channels 530, aligned to the Y direction, connect to reaction sites 520. Such channels 530 are referred to herein as Y-channels, and each reaction site has a corresponding Y-channel. Additionally, in at least one embodiment of the invention, a group of microfluidic channels runs along the X direction (herein referred to as X-channels), wherein the group can include channels 540 below pixel array and channels 550 above the pixel array. Further, in such an example embodiment of the invention, it is assumed that intersecting X- and Y-channels do not form a fluidic connection. To form a connection between intersecting X- and Y-channels, at least one embodiment of the invention includes implementing and/or using fluidic vias 560.

The fluidic networks corresponding to different reaction sites 1 . . . 4 (520) do not form fluidic connections. Accordingly, different chemistries 570 can be simultaneously delivered to different reaction sites within a single pixel. Alternatively, the same chemistry can be delivered to different reaction sites at different times, implementing time multiplexing, such as illustrated in FIG. 3 and FIG. 4.

Figure 6A:
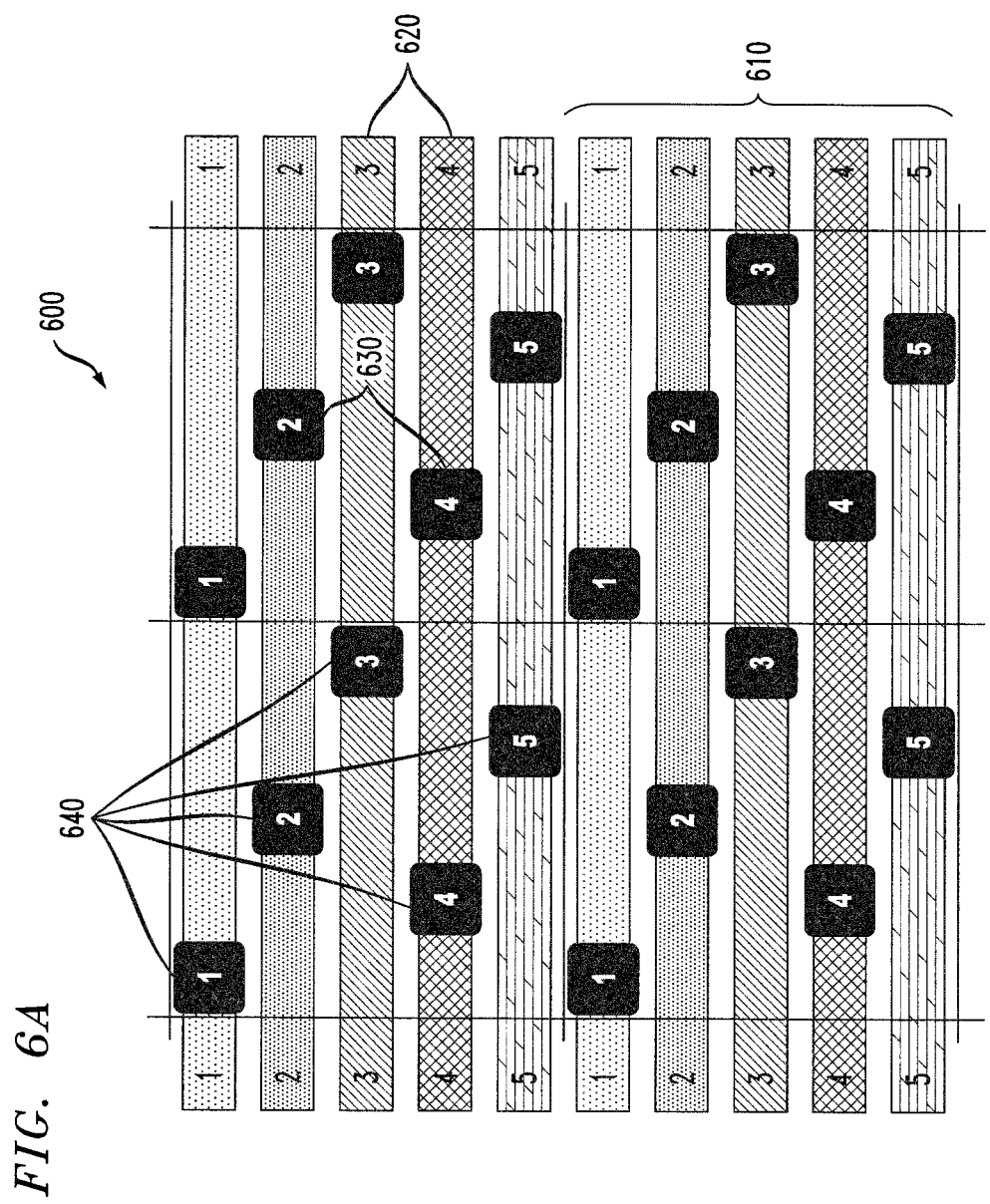
FIG. 6a is a diagram illustrating exemplary placement of reaction sites in a pixel using Gauss numbers, in accordance with an example embodiment of the invention.

FIG. 6a is a diagram illustrating exemplary placement of reaction sites in a pixel within a microarray 600 using Gauss numbers, in accordance with an example embodiment of the invention. By way of example, in an illustrative embodiment of the invention, the placement of reaction sites must satisfy the following properties:

1) Each pixel 610 has equal number of reaction sites n;
2) Each reaction site 640 is connected to the plane as illustrated in the figure to a microfluidic channel 620;
3) Microfluidic channels are parallel (either vertical or horizontal) and do not overlap; and
4) The minimum distance 630 between any two reaction sites 640 is maximized.

These four conditions lead to an optimization problem on integer lattices. This problem has an exact optimal solution wherein n is a Gaussian number, that is, when n represents a sum of two integer squares. By way of illustration, a list of such numbers for n≤30 is as follows: {1, 2, 4, 5, 8, 9, 13, 16, 17, 20, 25, 26, 29}. FIG. 6a provides an example of optimal reaction sites placement for n=5. The general solution for Gaussian case is as follows: Let $n=a^2+b^2$. By way of example, the following situations are possible:

1) a≠0 and b≠0. As such, the optimal lattice of site placements is given by the generator vectors (a/n, b/n) and (b/n, −a/n) on the pixel grid, and has a minimum distance of 1/√n pixels.
2) n is a perfect square. As such, the optimal lattice of site placements is given by the generator vectors (1, 0) and (1/√n, 1/n) on the pixel grid, and has a minimum distance of 1/√n pixels.

Figure 6B:
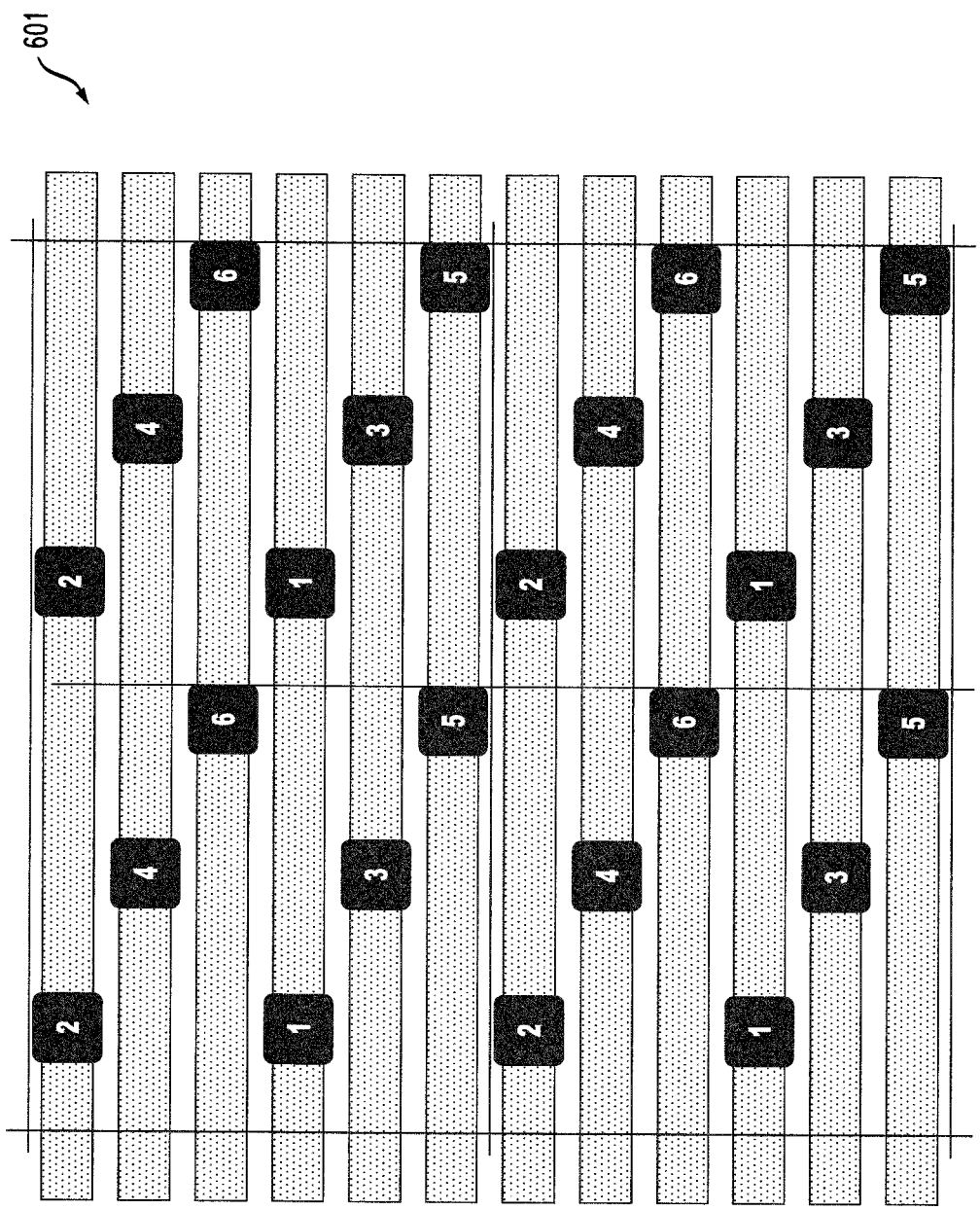
FIG. 6b is a diagram illustrating exemplary placement of reaction sites in a pixel using an approximate solution, in accordance with an example embodiment of the invention.

If n is not a Gaussian number, an approximate solution with a minimum distance sufficiently close to the optimal can be determined numerically by exhaustive search through the $n^4$ pairs of possible generating vectors which includes coordinates belonging to the set: {0, 1/n, 2/n, . . . , (n−1)/n}. This computation can be carried out, for example, on a computer for any n≤500. An example of an approximate solution for n=6 is illustrated in FIG. 6b. Accordingly, FIG. 6b is a diagram illustrating exemplary placement of reaction sites in a pixel within a microarray 601 using an approximate solution, in accordance with an example embodiment of the invention. In such an example, the minimum distance between any two reaction sites is d≈0.3727 pixels, which is approximately 8.71% smaller than the Gaussian case ideal solution, for which the minimum distance would be d=1/√6≈0.4082 pixels.

Figure 7:
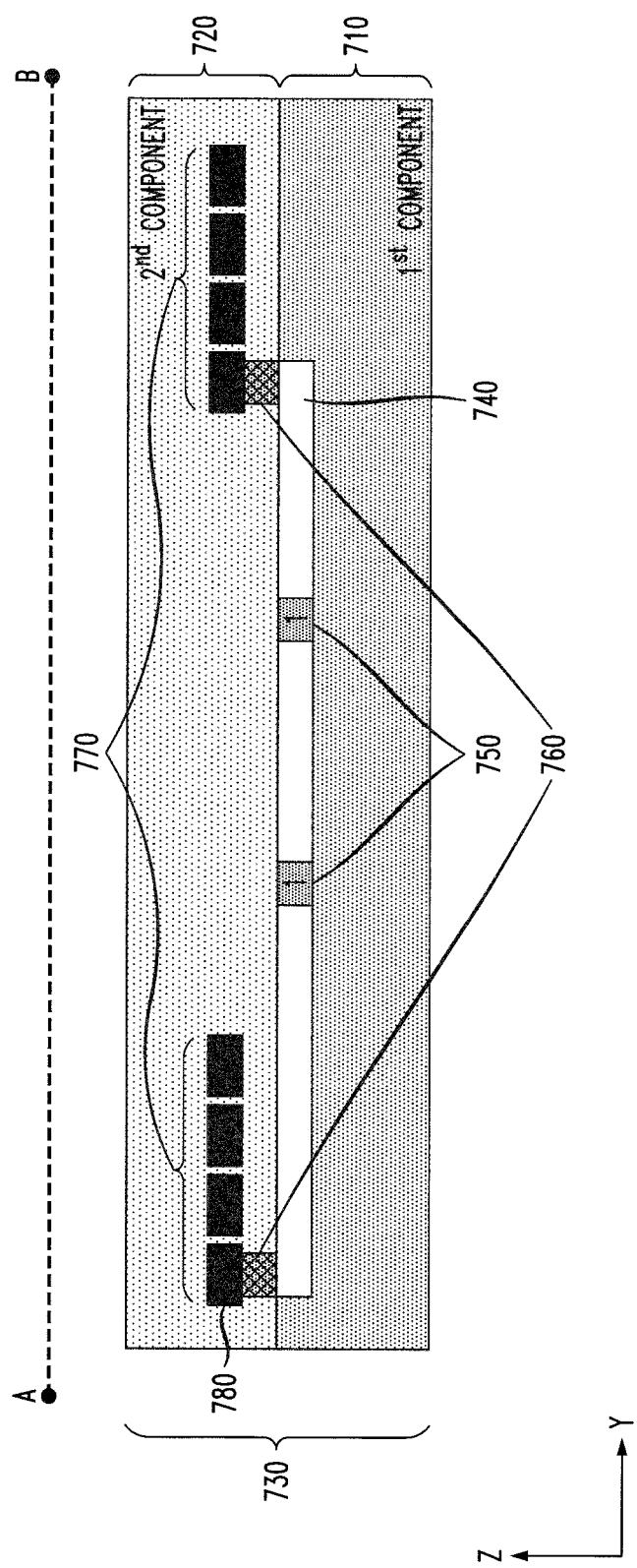
FIG. 7 is a diagram illustrating a side view of a two-component microarray, in accordance with an example embodiment of the invention.

As detailed herein, a pipelined microarray, in accordance with one or more embodiments of the invention, includes multiple unconnected fluidic networks. FIG. 7 is a diagram illustrating a side view of a two-component microarray, in accordance with an example embodiment of the invention. By way of illustration, FIG. 7 depicts one example embodiment of such networks as a cross-section along line AB (as also illustrated in FIG. 5). Two independently-made components, first component 710 and second component 720, are bonded to form microarray 730. Component 710 includes a surface microfluidic Y-channel 740, which connects reaction sites 750 with fluidic ports (vias) 760. As detailed herein, a reaction site (such as depicted by components 750 in FIG. 7) do not block the surface channel (such as channel 740), as each reaction site serves as a chemical modification of the channel. Component 720 includes sub-surface microfluidic X-channels 770. As illustrated in FIG. 7, only X-channels aligned with fluidic vias (also referred to herein as ports) 760 form a fluidic connection with Y-channel 740. Additionally, FIG. 7 depicts sub-surface channels 780 of the second component 720 that connect to surface channel 740 from the first component 710 through fluidic via 760.

An integrated microarray flow cell can also be fabricated using techniques such as described, by way merely of example, in U.S. application Ser. No. 13/920,226, filed on Jun. 18, 2013 and entitled "Nanochannel Process and Structure for Bio-Detection," which is incorporated by reference herein in its entirety.

Figure 8A:
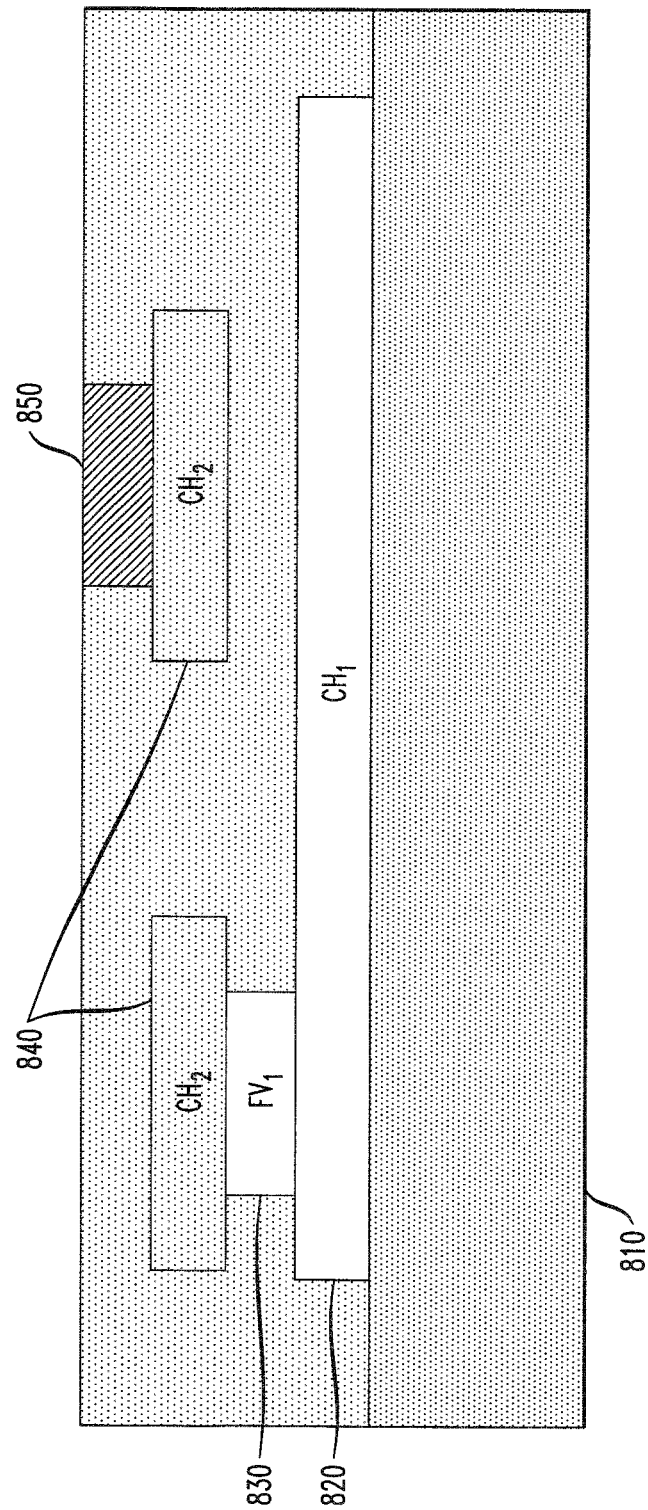
FIG. 8a is a diagram illustrating a cross-section view of an integrated microarray with two levels of fluidic channels, in accordance with an example embodiment of the invention.

FIG. 8a is a diagram illustrating a cross-section view of an integrated microarray with two levels of fluidic channels, in accordance with an example embodiment of the invention. Such a structure as illustrated in FIG. 8a can be fabricated, for example, on a glass, silicon, or other suitable substrate (such as further discussed below in connection with FIG. 8b). With a silicon substrate or other material which would be etched by $XeF_2$, first a protection layer 810 of silicon dioxide would be deposited. The first fluidic channel level 820 would be formed by depositing an amorphous or polycrystalline silicon layer of the desired channel height, patterning the silicon (Si) layer into the desired channel configuration by a combination of photolithography and reactive ion etching (ME), stripping the photoresist and over-coating with a (thick) $SiO_2$ layer.

The fluidic via layer 830 could then be formed by planarizing the oxide layer using chemical-mechanical polishing (CMP), either leaving the desired thickness of oxide over the Si pattern that will become the first fluidic channel level, or depositing additional oxide after the planarization step. Additionally, photolithography and ME can be used to remove the oxide layer over the first fluidic channel 820 where fluidic vias 830 are desired. The second fluidic channel level 840 is then formed by depositing an amorphous or polycrystalline silicon layer of the desired channel height and patterning the Si layer into the desired channel configuration by a combination of photolithography and ME. Another oxide layer can also be deposited and planarized.

Further, an additional photolithography step can be used in combination with RIE etching of the oxide down to the silicon to create the fill ports, reaction site openings 850, and vent holes. Fill ports are used to introduce and remove the chemistry which is provided during use of the microarray flow cell, and vent holes are temporary openings used during $XeF_2$ etching. Vapor phase etching of the Si with $XeF_2$ can be used to convert the Si structures into the integrated microarray flow cell. Also, an oxide deposition step can be performed to "pinch-off" and seal the vent holes. The dimensions of the reaction site openings 850 and fill ports, as well as the thickness of the final oxide deposition step, are selected to not close off either the reaction site openings 850 or the fill ports, while sealing the vent holes. For example, the reaction sites may be 0.5 microns on a side, the fill ports may be 2 millimeters (mm) in diameter, and the vent holes may be 0.1 microns on a side; accordingly, an oxide layer 0.1 microns thick would seal the vent holes, but not the other noted features. Further description of fill ports and vent holes can be found, by way of example, in U.S. application Ser. No. 13/920,226, filed on Jun. 18, 2013 and entitled "Nanochannel Process and Structure for Bio-Detection," which is incorporated by reference herein in its entirety.

Figure 8B:
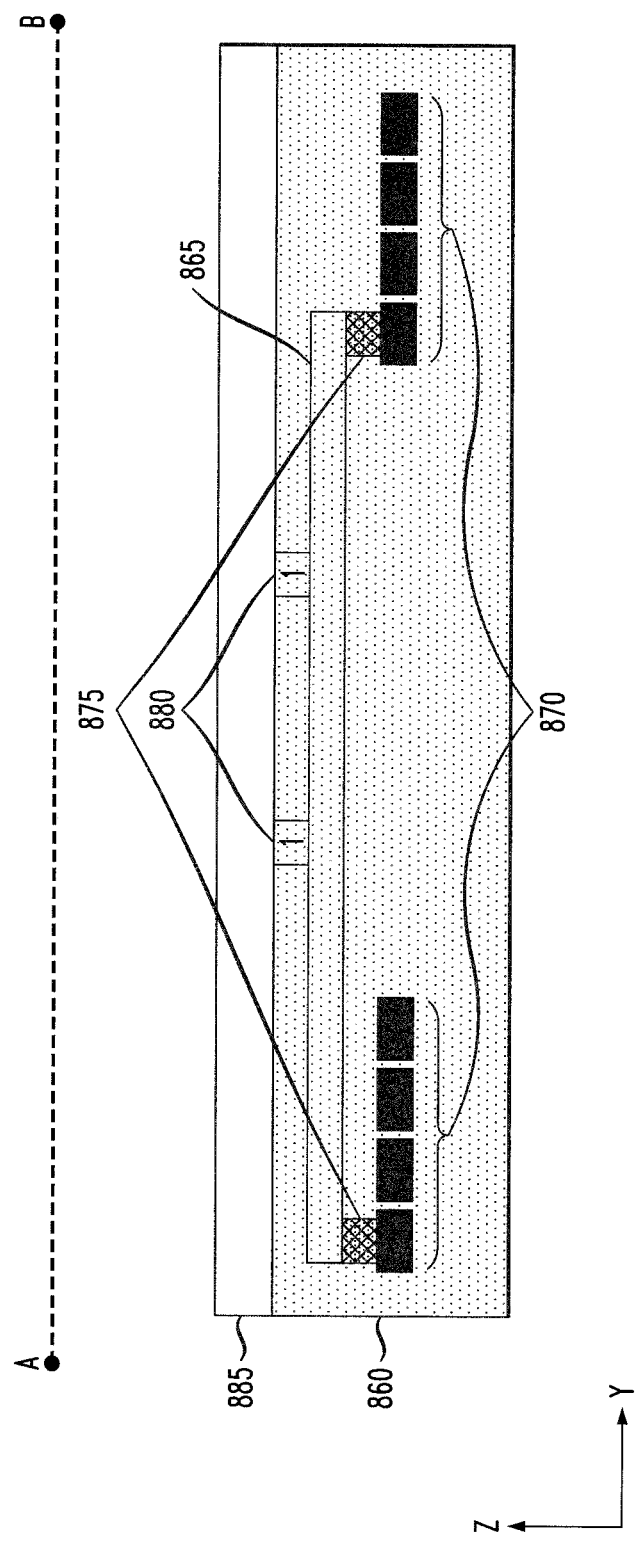
FIG. 8b is a diagram illustrating a side view of an integrated fluidic cell with two level fluidic channels, in accordance with an example embodiment of the invention.

With the fabrication of an integrated microarray with two levels of fluid channels described, a side view of such a microarray is shown in FIG. 8b. As further detailed herein, FIG. 8b depicts one example embodiment of such a microarray as a cross-section along line AB (as also illustrated in FIG. 5). By way of illustration, FIG. 8b depicts an integrated (single component) microarray 860 with two levels of fluid channels: X-channels 870 and Y-channel 865. As depicted in FIG. 8b, the integrated microarray 860 also includes fluid (or gaseous) vias 875 positioned so as to form a connection between the X-channels 870 and the Y-channel 865. Further, the integrated microarray 860 additionally includes reaction site openings 880, as well as a cover 885 (for example, a glass cover) which may include a sealing polymer.

Accordingly, a number of options can be implemented to provide the necessary or desired material at the reaction site openings 880. For example, one option is to deposit, on a cover glass 885, the desired materials in the pattern shown in FIG. 6a and/or FIG. 6b, and to then align the active regions with the reaction site openings 880 down to the Y-channel 865 in the integrated microarray 860. The cover glass 885 can be temporally or permanently secured to the integrated microarray 860 to seal the reaction site openings 880.

If a temporary seal is used, the microarray can be reused. An example embodiment of the invention includes using a thin compliant polymer layer on the cover glass 885 under the active materials so that a seal is formed when the cover glass 885 is compressed against the microarray 860. The thickness of the cover glass can be, for example, on the order of hundreds of micrometers (μm), and the thickness of a compliant polymer will depend on the surface's flatness and can range from a few to tens of microns. Note, as detailed above, that each reaction site can be comprised of an array of reaction site openings so that an array of reaction sites is formed even though the material provided on the cover glass is not patterned into a fine array. An alternate technique can include, for example, dissolving the necessary material into a wax or polymer that could be dispensed as a liquid, which would wick into the reaction site openings and seal the openings.

Figure 9:
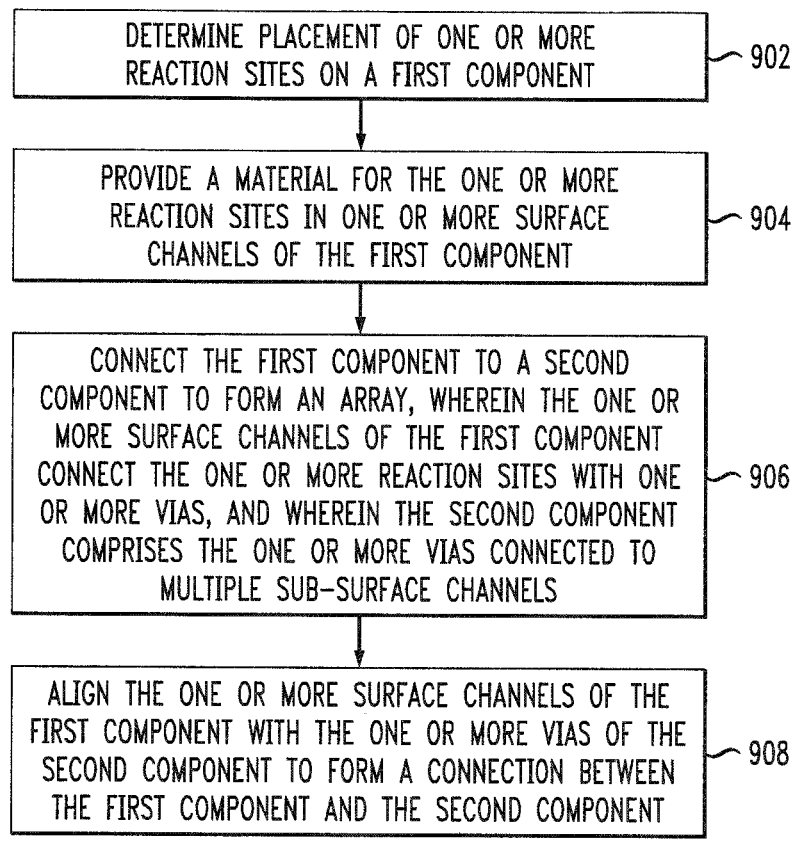
FIG. 9 is a flow diagram illustrating techniques according to an embodiment of the invention.

FIG. 9 is a flow diagram illustrating techniques according to an embodiment of the invention. Step 902 includes determining placement of one or more reaction sites on a first component. The determining step can be based on use of a Gauss number if the number of the one or more reaction sites represents a sum of two integer squares and/or based on use of numerical approximation.

Step 904 includes providing a material for the one or more reaction sites in one or more surface channels of the first component. Step 906 includes connecting the first component to a second component to form an array, wherein the one or more surface channels of the first component connect the one or more reaction sites with one or more vias, and wherein the second component comprises the one or more vias connected to multiple sub-surface channels. Step 908 includes aligning the one or more surface channels of the first component with the one or more vias of the second component to form a connection between the first component and the second component.

Also, the techniques depicted in FIG. 9 can include independently delivering chemical matter to each of the multiple reaction sites.

As also detailed herein, at least one embodiment of the invention includes an apparatus that includes an array comprising one or more pixels, wherein each of the one or more pixels comprises one or more reaction sites. Location of the one or more reaction sites on each of the one or more pixels can be based, for example, on utilization of one or more Gauss numbers. The apparatus also includes a network comprising (i) a set of one or more surface channels in a first component of the array, and (ii) a set of two or more sub-surface channels in a second component of the array, wherein each reaction site corresponds to a channel from the set of one or more surface channels, and wherein said set of two or more sub-surface channels comprises one or more sub-surface channels proximate to a first portion of the array and one or more sub-surface channels proximate to a second portion of the array. The apparatus further includes multiple vias in the second component of the array connecting each channel from the set of one or more surface channels to (i) one of the one or more sub-surface channels proximate to the first portion of the array and (ii) one of the one or more sub-surface channels proximate to the second portion of the array.

As detailed herein, the network can specifically include a set of one or more fluidic channels and a set of two or more fluidic channels, and wherein said multiple vias comprise multiple fluidic vias. Similarly, at least one embodiment of the invention can also include a network that includes a set of one or more gaseous channels and a set of two or more gaseous channels, and wherein said multiple vias comprise multiple gaseous vias.

Additionally, in such an apparatus, the size of each of the multiple pixels is based on an optical resolution of an imaging device associated with the apparatus. By way of example, the size of each of the multiple pixels can be approximately one micrometer, or can be greater than one micrometer. Further, in at least one embodiment of the invention, each of the multiple pixels includes an equal number of reaction sites.

Also, in at least one embodiment of the invention, the one or more surface channels are parallel and do not overlap, the two or more sub-surface channels are parallel and do not overlap, and the set of one or more surface channels runs perpendicular to the set of two or more sub-surface channels.

Figure 10:
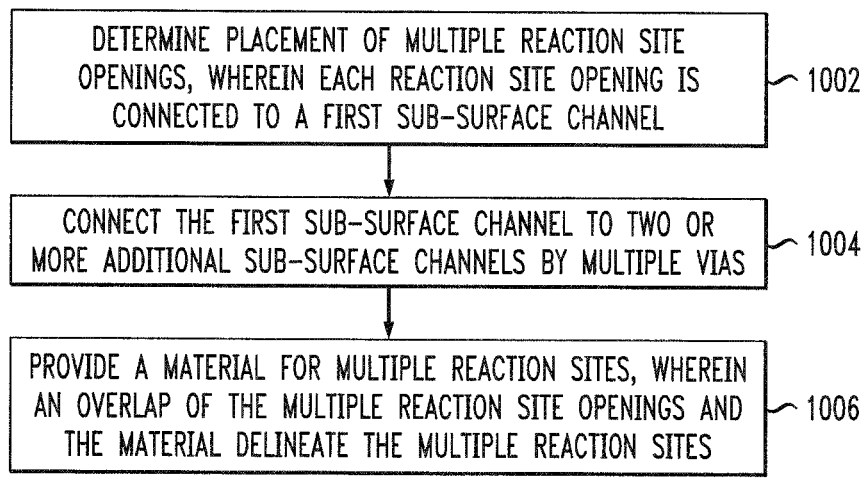
FIG. 10 is a flow diagram illustrating techniques according to an embodiment of the invention.

FIG. 10 is a flow diagram illustrating techniques according to an embodiment of the present invention. Step 1002 includes determining placement of multiple reaction site openings, wherein each reaction site opening is connected to a first sub-surface channel. The determining step can be based on use of a Gauss number if the number of the multiple reaction site openings represents a sum of two integer squares and/or based on use of numerical approximation.

Step 1004 includes connecting the first sub-surface channel to two or more additional sub-surface channels by multiple (fluidic) vias. Step 1006 includes providing a material for multiple reaction sites, wherein an overlap of the multiple reaction site openings and the material delineate the multiple reaction sites.

The techniques depicted in FIG. 10 can also include incorporating a cover to seal the multiple reaction site openings. The cover can include, for example, a glass cover with or without a sealing polymer. Additionally, incorporating the cover can include temporarily securing the cover or permanently securing the cover. Also, the techniques depicted in FIG. 10 can include independently delivering chemical matter to each of the multiple reaction sites.

Additionally, at least one embodiment of the invention includes an apparatus that includes an array comprising one or more pixels, wherein each of the one or more pixels comprises multiple reaction sites openings, and a first set of one or more sub-surface channels, wherein each of the multiple reaction site openings is connected to a sub-surface channel from the first set of one or more sub-surface channels. The apparatus additionally includes a second set of two or more sub-surface channels, and multiple vias connecting each channel from the first set of one or more sub-surface channels to (i) a first sub-surface channel from the second set of two or more sub-surface channels and (ii) a second sub-surface channel from the second set of two or more sub-surface channels. Such an apparatus can additionally include a cover secured (temporarily or permanently) to the apparatus. The cover can include, for example, a glass cover with or without a sealing polymer.

In such an apparatus, each of the pixels is configured to independently receive chemical matter at each of the multiple reaction site openings. Additionally, the size of each pixel can be based on an optical resolution of an imaging device associated with the apparatus. Further, in such an apparatus, each of the multiple reaction sites openings can include an array of multiple openings, and the location of each of the multiple reaction sites openings on each of the one or more pixels can be based on utilization of one or more Gauss numbers.

Figure 11:
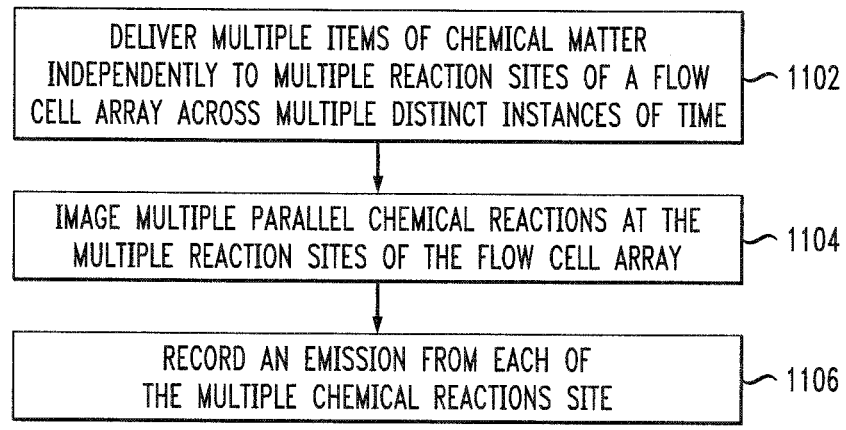
FIG. 11 is a flow diagram illustrating techniques according to an embodiment of the invention.

FIG. 11 is a flow diagram illustrating techniques according to an embodiment of the invention. Step 1102 includes delivering multiple items of chemical matter independently to multiple reaction sites of a flow cell array across multiple distinct instances of time. The multiple distinct instances of time can include multiple non-overlapping instances of time determined based on the multiple parallel chemical reactions and/or based on the multiple items of chemical matter.

Step 1104 includes imaging multiple parallel chemical reactions at the multiple reaction sites of the flow cell array. The multiple parallel chemical reactions can include, for example, multiple instances of biological sequencing (such as DNA sequencing). Step 1106 includes recording an emission from each of the multiple chemical reactions site.

The techniques depicted in one or more of the above-detailed flow diagrams can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an aspect of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in one or more of the above-detailed flow diagrams can be implemented via a computer program product that can include computer useable program code that is stored in a computer readable storage medium in a data processing system, and wherein the computer useable program code was downloaded over a network from a remote data processing system. Also, in an aspect of the invention, the computer program product can include computer useable program code that is stored in a computer readable storage medium in a server data processing system, and wherein the computer useable program code is downloaded over a network to a remote data processing system for use in a computer readable storage medium with the remote system.

An aspect of the invention or elements thereof can be implemented in the form of an apparatus including a memory and at least one processor that is coupled to the memory and configured to perform exemplary method steps.

Figure 12:
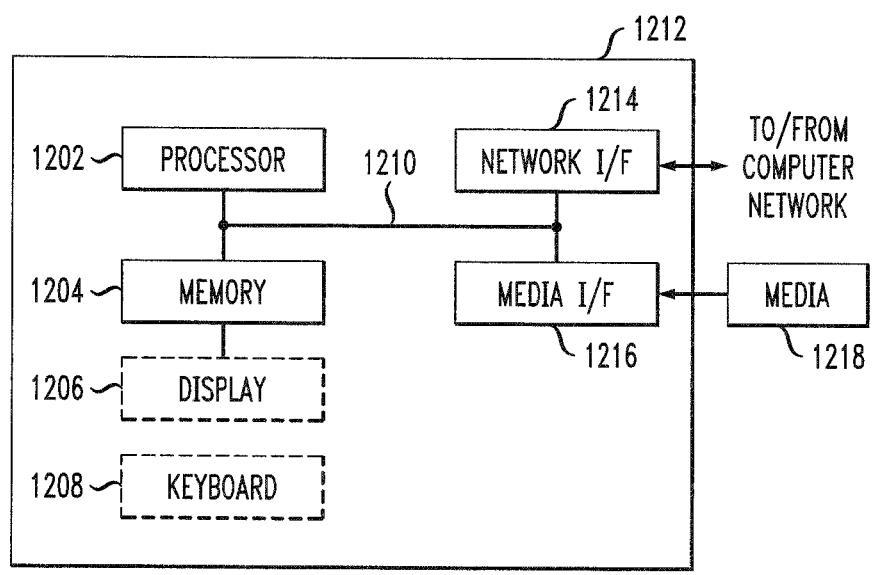
FIG. 12 is a system diagram of an exemplary computer system on which at least one embodiment of the invention can be implemented.

Additionally, an aspect of the present invention can make use of software running on a general purpose computer or workstation. With reference to FIG. 12, such an implementation might employ, for example, a processor 1202, a memory 1204, and an input/output interface formed, for example, by a display 1206 and a keyboard 1208. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 1202, memory 1204, and input/output interface such as display 1206 and keyboard 1208 can be interconnected, for example, via bus 1210 as part of a data processing unit 1212. Suitable interconnections, for example via bus 1210, can also be provided to a network interface 1214, such as a network card, which can be provided to interface with a computer network, and to a media interface 1216, such as a diskette or CD-ROM drive, which can be provided to interface with media 1218.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 1202 coupled directly or indirectly to memory elements 1204 through a system bus 1210. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 1208, displays 1206, pointing devices, and the like) can be coupled to the system either directly (such as via bus 1210) or through intervening I/O controllers (omitted for clarity).

Network adapters such as network interface 1214 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 1212 as shown in FIG. 12) running a server program. It will be understood that such a physical server may or may not include a di splay and keyboard.

As will be appreciated by one skilled in the art, aspects of the present invention may be embodied as a system, method and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, as noted herein, aspects of the present invention may take the form of a computer program product that may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 1202. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed general purpose digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of another feature, integer, step, operation, element, component, and/or group thereof.

The corresponding structures, materials, acts, and equivalents of all means or step plus function elements in the claims below are intended to include any structure, material, or act for performing the function in combination with other claimed elements as specifically claimed.

At least one aspect of the present invention may provide a beneficial effect such as, for example, increasing the density of chemical reactions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    positioning multiple reaction sites in a first set of surface channels within a physical element flow cell array, wherein the first set of surface channels are aligned to a first direction, and wherein positioning comprises positioning the multiple physical reaction sites within the first set of surface channels such that a distance between each of the multiple physical reaction sites is smaller than an optical resolution perpendicular to the optical path of a given fluorescence microscope, and wherein the distance is less than one micron;
    connecting the first set of surface channels to a second set of surface channels by multiple vias, wherein the second set of surface channels are aligned to a second direction;
    establishing a designation wherein pairs of surface channels within the second set are designated for use with (i) a distinct one of multiple chemical matters, (ii) one or more reaction sites, among the multiple reaction sites, designated for use with the distinct one of the multiple chemical matters, and (iii) one or more surface channels within the first set connected to the one or more reaction sites designated for use with the distinct one of the multiple chemical matters;
    delivering, within at least a portion of the physical element flow cell array, the multiple chemical matters to the multiple reaction sites;
    imaging, subsequent to said delivering, multiple parallel chemical reactions at the multiple reaction sites using the given fluorescence microscope, wherein the multiple parallel chemical reactions comprise multiple instances of biological sequencing, and wherein the distance between two or more of the multiple reaction sites being imaged simultaneously is greater than the optical resolution of the given fluorescence microscope while the distance between two or more of the other multiple physical reaction sites is less than the optical resolution of the given fluorescence microscope and less than one micron; and
    incorporating a cover in connection with the multiple reaction sites.

2. The method of claim 1, wherein said incorporating comprises securing the cover.

* * * * *